United States Patent
Han et al.

(10) Patent No.: US 12,085,528 B2
(45) Date of Patent: Sep. 10, 2024

(54) APPARATUS AND METHOD FOR SEPARATING SINGLE CELLS

(71) Applicant: INJE UNIVERSITY INDUSTRY-ACADEMIC COOPERATION FOUNDATION, Gimhae-si (KR)

(72) Inventors: Ki-Ho Han, Busan (KR); Jin-Ho Kim, Busan (KR)

(73) Assignee: INJE UNIVERSITY INDUSTRY—ACADEMIC COOPERATION FOUNDATION, Gimhae-si (KR)

( * ) Notice: Subject to any disclaimer, the term of this patent is extended or adjusted under 35 U.S.C. 154(b) by 1560 days.

(21) Appl. No.: 16/311,619

(22) PCT Filed: May 14, 2015

(86) PCT No.: PCT/KR2015/004857
§ 371 (c)(1),
(2) Date: Jan. 28, 2019

(87) PCT Pub. No.: WO2016/076494
PCT Pub. Date: May 19, 2016

(65) Prior Publication Data
US 2019/0227021 A1  Jul. 25, 2019

(30) Foreign Application Priority Data
Nov. 13, 2014  (KR) .................. 10-2014-0158232

(51) Int. Cl.
*G01N 27/30* (2006.01)
*B01L 3/00* (2006.01)
(Continued)

(52) U.S. Cl.
CPC ........ *G01N 27/30* (2013.01); *B01L 3/502715* (2013.01); *B01L 3/50273* (2013.01);
(Continued)

(58) Field of Classification Search
CPC .... G01N 27/30; G01N 15/10; G01N 15/1459; G01N 2015/0065; G01N 2015/1062;
(Continued)

(56) References Cited

U.S. PATENT DOCUMENTS

2003/0209059 A1* 11/2003 Kawano ............ B01L 3/502784
73/53.01
2005/0023137 A1* 2/2005 Bhullar .................... C12M 1/00
422/82.01
(Continued)

FOREIGN PATENT DOCUMENTS

KR  10-2011-0009422 A  1/2011
KR  10-2011-0037345 A  4/2011
(Continued)

OTHER PUBLICATIONS

Tehranirokh et al., "Microfluidic devices for cell cultivation and proliferation", 2013, Biomicrofluidics 7, 051502 (Year: 2013).*
(Continued)

*Primary Examiner* — Samuel P Siefke
*Assistant Examiner* — Henry H Nguyen
(74) *Attorney, Agent, or Firm* — FisherBroyles LLP

(57) ABSTRACT

An apparatus and method for separating single cells. The apparatus includes: a fluid channel having an upper panel, a lower panel, and a flow path formed therebetween that is configured to convey a sample including a single cell; a single cell measuring unit including first and second electrodes provided on the fluid channel in a predetermined spaced relationship for applying electrical signals to the sample in the flow path, and a detection electrode provided
(Continued)

between the first and second electrodes to detect the single cell in the sample in the flow path, such that the single cell measuring unit applies the electrical signals to the sample in the flow path, detects the electrical signals of the sample, and detects whether there is the single cell in the sample; and a single cell separation control device which outputs a single cell separation control signal when the single cell is detected by the detection electrode.

11 Claims, 12 Drawing Sheets

(51) Int. Cl.
  *B01L 3/02* (2006.01)
  *C12M 1/00* (2006.01)
  *C12M 1/34* (2006.01)
  *C12M 1/42* (2006.01)
  *G01N 15/01* (2024.01)
  *G01N 15/10* (2024.01)
  *G01N 15/14* (2024.01)

(52) U.S. Cl.
  CPC ... *B01L 3/502753* (2013.01); *B01L 3/502761* (2013.01); *C12M 1/34* (2013.01); *C12M 1/42* (2013.01); *C12M 47/04* (2013.01); *G01N 15/10* (2013.01); *B01L 3/0241* (2013.01); *B01L 2200/0642* (2013.01); *B01L 2200/0668* (2013.01); *B01L 2300/0645* (2013.01); *B01L 2300/0654* (2013.01); *B01L 2400/0487* (2013.01); *G01N 15/01* (2024.01); *G01N 2015/1024* (2024.01); *G01N 2015/1029* (2024.01); *G01N 15/1459* (2013.01)

(58) Field of Classification Search
  CPC ........ G01N 2015/1087; G01N 15/1031; B01L 3/502715; B01L 3/50273; B01L 3/502753; B01L 3/502761; B01L 3/0241; B01L 2200/0642; B01L 2200/0668; B01L 2300/0645; B01L 2300/0654; B01L 2400/0487; C12M 1/34; C12M 1/42; C12M 47/04
  See application file for complete search history.

(56) References Cited

U.S. PATENT DOCUMENTS

| | | | |
|---|---|---|---|
| 2008/0283402 A1* | 11/2008 | Peach | B03C 5/026 204/547 |
| 2012/0103813 A1* | 5/2012 | Sato | B03C 5/026 204/547 |
| 2012/0184010 A1 | 7/2012 | Medoro et al. | |
| 2013/0256197 A1* | 10/2013 | Katsumoto | G01N 15/12 209/127.1 |
| 2014/0248621 A1* | 9/2014 | Collins | G01N 33/4833 435/6.12 |

FOREIGN PATENT DOCUMENTS

| | | | | |
|---|---|---|---|---|
| KR | 10-0787234 B1 | 12/2012 | | |
| KR | 10-2014-0091640 A | 7/2014 | | |
| WO | WO-2007092713 A2 * | 8/2007 | ........ | B01L 3/502761 |
| WO | WO-2012178166 A1 * | 12/2012 | ........ | B01L 3/502761 |
| WO | WO-2014107812 A1 * | 7/2014 | ........ | B01L 3/502715 |

OTHER PUBLICATIONS

Huang, Nien-Tsu et al., "Recent advancements in optofluidics-based sing-cell analysis: optical on-chip cellular manipulation, treatment, and property detection," The Royal Society of Chemistry: Lab Chip, vol. 14, No. 7, pp. 1217-1378, Apr. 7, 2014.

Han, Song-I et al., "Deterministic Lateral Displacement as a Function of Particle Size Using a Piecewise Curved Planar Interdigitated Electrode Array," The Korean Society of Mechanical Engineers, pp. 241-249, 2012, with English abstract.

* cited by examiner

Patterning

Au etching

Cr etching & Drilling

PDMS Pour & curing

Replica of PDMS

Bottom & Top Bonding

FIG. 14A
FIG. 14B
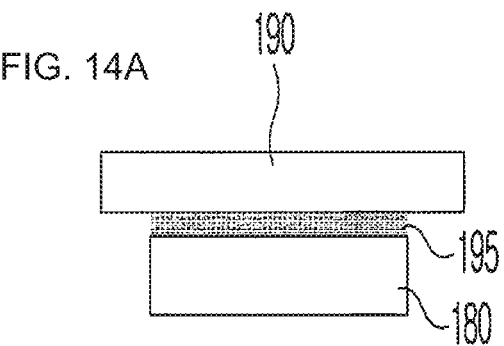

BLUE=BUFFER
GREEN=CELL

APPARATUS AND METHOD FOR SEPARATING SINGLE CELLS

CROSS REFERENCE TO RELAYED APPLICATIONS AND CLAIM OF PRIORITY

This patent application is a National Phase application under 35 U.S.C. § 371 of International Application No. PCT/KR2015/004857, filed May 14, 2015, which claims priority to Korean Patent Application No. 10-2014-0158232 filed Nov. 13, 2014, entire contents of which are incorporated herein by reference.

TECHNICAL FIELD

The present invention relates to an apparatus and a method for separating single cells, and particularly, to an apparatus and a method for separating single cells which measure the number of single cells passing through a channel by using a structure of a fine fluid chip and discharge the single cells to the outside by introducing the single cells into fluid droplets based on a measurement result.

BACKGROUND ART

Cells maintain vital phenomena by performing various biological functions such as gene expression, cell growth, cell cycles, metabolism, signal transmission, and the like through various and complex protein-protein interactions.

In the case of most research methodologies regarding cell groups used for biological studies, data analyses are performed on the assumption that separate cells in the cell group perform uniform cell reactions. However, if the separate cells do not actually perform the uniform reactions, result analyses, which are performed based on average measured values, may cause errors. Whether the separate cells actually perform the uniform reactions has been extremely less proven experimentally due to various technical problems, and as a result, development on a technology for analyzing single cells is essentially required.

As a method using a micro-array for analyzing single cells in the related art, there are a method which forms a hole having a size similar to a size of a cell so that the single cell is introduced into the hole, and a method which captures the single cell at a particular position by using dielectrophoresis. The dielectrophoresis has a problem in that the cell moves to undesired other positions when a supply of a voltage is cut off.

In addition, there is a method called an electrical rotation for measuring a dielectric property of the single cell. This method is a method that measures a rotation rate by applying rotational alternating current signals having a phase difference of 360/n to n electrodes, and compares and analyzes the measurement result and a theoretical result regarding a rotational speed spectrum of the cell based on a single-shell dielectric model, thereby deriving the dielectric property of the cell.

In the related art, to measure the rotational speed spectrum of the cell as described above, four electrodes in the form of a crisscross are formed on a bottom substrate, a cell to be measured is positioned at a center of the electrodes, and ROT signals, which make the cell rotation and have phase differences of 90 degrees, are applied to the electrodes, respectively. In this method, the cell is positioned at the center of the electrodes by generating nDEP force on the four electrodes before the rotational speed spectrum of the cell is measured.

However, the method in the related art has a problem in that there may occur interference between the cells as undesired cells are introduced to a measurement region, the center of the electrodes, during the process of measuring the rotational speed spectra of the cells, and has a problem in that friction occurs between a cell membrane and the bottom substrate while the cell rotates. The method in the related art also has a problem in that in a case in which a frequency of the rotational alternating current signal is increased during the electrical rotation, positive dielectrophoretic force is applied to the cell, that is, force is generated toward the electrodes, such that the cell adheres to the electrode, and as a result, it is difficult to accurately measure the rotational speed spectrum.

DISCLOSURE

Technical Problem

The present invention has been made in an effort to solve the aforementioned problems, and an object of the present invention is to provide an apparatus and a method for separating single cells which measure the number of single cells passing through a channel by using a structure of a fine fluid chip and discharge the single cells to the outside by introducing the single cells into fluid droplets based on a measurement result.

Another object of the present invention is to provide an apparatus and a method for separating single cells in which a buffer unit is provided between an electrical measurement unit and a separation unit in order to prevent a reverse flow (backflow) from occurring due to pressure used to separate the single cell from a sample including the single cell.

Still another object of the present invention is to provide an apparatus and a method for separating single cells which separate and discharge heterologous cells and single cells, which are desired cells, and allow the discharged single cells to be independently separated and stored in respective spaces of a well plate having the multiple spaces.

Technical Solution

A single cell separating apparatus according to an exemplary embodiment of the present invention may include: a fluid channel which has an upper panel and a lower panel and has a flow path which is formed between the upper panel and the lower panel and configured to convey a sample including a single cell; a single cell measuring unit which includes first and second electrodes which are provided on the fluid channel so as to be spaced apart from each other at a predetermined interval and apply electrical signals to the sample being conveyed through the flow path of the fluid channel, and a detection electrode which is provided between the first electrode and the second electrode and detects the single cell in the sample being conveyed through the flow path, such that the single cell measuring unit applies the electrical signals to the sample being conveyed through the flow path, detects the electrical signals of the sample to which the electrical signals are applied, and detects whether there is the single cell in the sample; and a single cell separation control device which outputs a single cell separation control signal when the single cell is detected by the detection electrode.

A single cell separating apparatus according to another exemplary embodiment of the present invention may include: a fluid channel which has an upper panel and a lower panel and has a flow path which is formed between the upper panel and the lower panel and configured to convey a sample including a single cell; a single cell measuring unit which includes an optical measurement sensor for emitting light to the fluid channel and allows the optical measurement sensor to receive light reflected by the sample including the single cell, convert the light into an electrical signal, and output the electrical signal as a single cell detection signal; and a single cell separation control device which derives a fluid channel passing speed of the sample including the single cell by using the electrical signal outputted from the optical measurement sensor, and outputs the single cell separation control signal based on the passing speed of the sample.

A single cell separating apparatus according to still another exemplary embodiment of the present invention may include: a fluid channel which has an upper panel and a lower panel and has a flow path which is formed between the upper panel and the lower panel and configured to convey a sample including a single cell; a single cell measuring unit which includes a Hall sensor for applying a magnetic field to the fluid channel and allows the Hall sensor to detect a voltage generated by the magnetic field and output the voltage; and a single cell separation control device which derives a fluid channel passing speed of the sample including the single cell by receiving the voltage detected by the Hall sensor, and outputs the single cell separation control signal based on the passing speed of the sample.

In the exemplary embodiment related to the present invention, the first electrode and the second electrode may be provided on the upper panel, the lower panel, or the upper and lower panels of the fluid channel.

In the exemplary embodiment related to the present invention, the single cell separation control device may count and provide the number of single cells passing through the flow path based on the electrical signal inputted from the detection electrode.

In the exemplary embodiment related to the present invention, the single cell separating apparatus may further include a single cell separating unit which supplies a fluid in response to the cell separation control signal of the single cell separation control device, couples the fluid to the single cell being conveyed to a cell discharge port, and discharges the single cell through the single cell discharge port.

In the exemplary embodiment related to the present invention, the single cell separating apparatus may further include a fluid supply unit which is operated by the single cell separation control signal of the single cell separation control device and supplies the fluid to be coupled to the single cell separated from the single cell separating unit.

In the exemplary embodiment related to the present invention, the single cell separating unit may supply the fluid to be coupled to the single cell by using air pressure.

In the exemplary embodiment related to the present invention, the single cell separating apparatus may further include a buffer unit which reduces a reverse flow caused by the air pressure created when supplying the fluid to be coupled to the single cell.

In the exemplary embodiment related to the present invention, the buffer unit may have a long flow path having a particular shape.

In the exemplary embodiment related to the present invention, the single cell separating apparatus may further include: a heterologous cell discharge channel which has one end portion connected to the fluid channel and discharges a heterologous cell to the outside when the heterologous cell is detected in the fluid channel by the single cell measuring unit; and a valve channel which has one end portion provided in the heterologous cell discharge channel and the other end portion connected to an air injecting unit for injecting air into the heterologous cell discharge channel.

In the exemplary embodiment related to the present invention, the fluid channel and the heterologous cell discharge channel may have different tube thicknesses.

In the exemplary embodiment related to the present invention, a PDMS membrane may be formed between the heterologous cell discharge channel and the valve channel.

In the exemplary embodiment related to the present invention, the single cell separating apparatus may further include a well plate driving unit which moves a well plate forward or rearward in response to the single cell separation control signal of the single cell separation control device.

In the exemplary embodiment related to the present invention, the well plate may have multiple spaces, a first space may store heterologous cells, and the remaining multiple spaces may separate and store the single cells, one space for each single cell.

A method of separating a single cell by using the single cell separating apparatus according to the exemplary embodiment of the present invention may include: injecting a sample including a single cell into a sample injecting unit of a fluid channel for injecting the sample; applying an electrical signal to the sample being conveyed through a flow path of the fluid channel; determining whether the single cell is present by detecting an electrical signal of the sample to which the electrical signal is applied; and supplying a fluid to be coupled to the single cell when the single cell is present, positioning the single cell in the fluid, and discharging the single cell through a single cell discharge port.

In the exemplary embodiment related to the present invention, the method may further include counting the number of single cells when the single cell is present, and providing the number of single cells separated from the corresponding sample.

Advantageous Effects

According to the present invention, the number of single cells passing through a channel is measured by using a structure of a fine fluid chip, and the single cell is separated based on the measurement result, and the single cell is introduced into a fluid droplet and discharged to the outside, such that it is possible to effectively separate the single cell from the sample including unit cells within a short time.

In addition, according to the present invention, the buffer unit is provided between the electrical measurement unit and the separation unit to prevent a reverse flow (backflow) caused by pressure used to separate the single cell from the sample including the single cells, such that it is possible to prevent abnormality caused by the reverse flow when electrical measurement is performed to separate the single cell in the electrical measurement unit.

In addition, according to the present invention, the heterologous cells and the single cells, which are desired cells, are separated and discharged, and the discharged single cells are independently separated and stored in the respective spaces of the well plate including the multiple spaces, such that it is possible to prevent purity from deteriorating due to the heterologous cells, and it is possible to prevent errors of resulting values caused by DNA amplification of the heterologous cells when gene analyses are performed in the future.

DESCRIPTION OF DRAWINGS

FIGS. 14A-14B are a view for explaining a PDMS membrane adopted in the present invention.

MODES OF THE INVENTION

Figure 1:
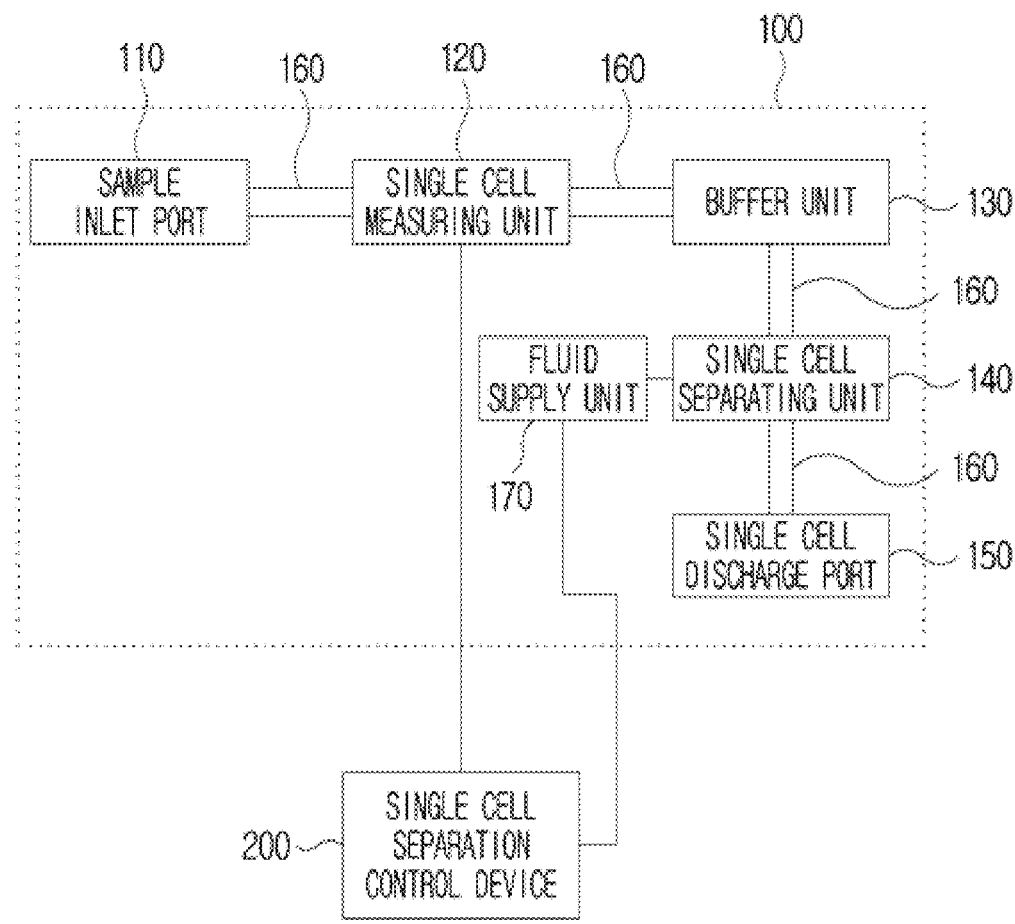
FIG. 1 is a block diagram for explaining a configuration of a single cell separating apparatus according to the present invention.

It should be noted that technical terms used in the present invention are used to just describe a specific embodiment and do not intend to limit the present invention. Further, unless the technical terms used in the present invention are particularly defined as other meanings in the present invention, the technical terms should be appreciated as meanings generally appreciated by those skilled in the art and should not be appreciated as excessively comprehensive meanings or excessively reduced meanings. Further, when the technical term used in the present invention is a wrong technical term that does not accurately express the spirit of the present invention, the technical term should be understood by being substituted by a technical term which can be correctly understood by those skilled in the art. In addition, a general term used in the present invention should be interpreted as defined in a dictionary or contextually, and should not be interpreted as an excessively reduced meaning.

In addition, singular expressions used in the present specification include plural expressions unless they have definitely opposite meanings in the context. It should not be interpreted that the terms "comprises," "comprising," "includes" and/or "including," used herein necessarily include all of the several constituent elements or several steps disclosed in the present invention, and it should be interpreted that the terms may not include some of the constituent elements or steps and may further include additional constituent elements or steps.

Hereinafter, the exemplary embodiments according to the present invention will be described in detail with reference to the accompanying drawings. The same or corresponding constituent elements are assigned with the same reference numerals regardless of reference numerals, and the repetitive description thereof will be omitted.

In addition, in the description of the present invention, the specific descriptions of publicly known related technologies will be omitted when it is determined that the specific descriptions may obscure the subject matter of the present invention.

In addition, it should be noted that the accompanying drawings are provided only to allow those skilled in the art to easily understand the spirit of the present invention, and the spirit of the present invention is not limited by the accompanying drawings.

Figure 2:
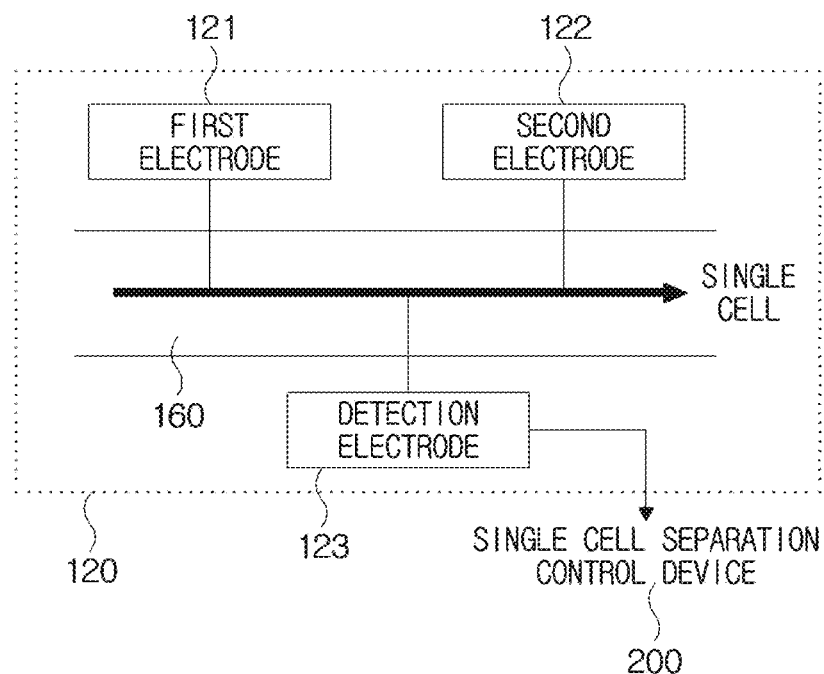
FIG. 2 is a block diagram for explaining an exemplary embodiment of a single cell separating unit in FIG. 1.
Figure 3:
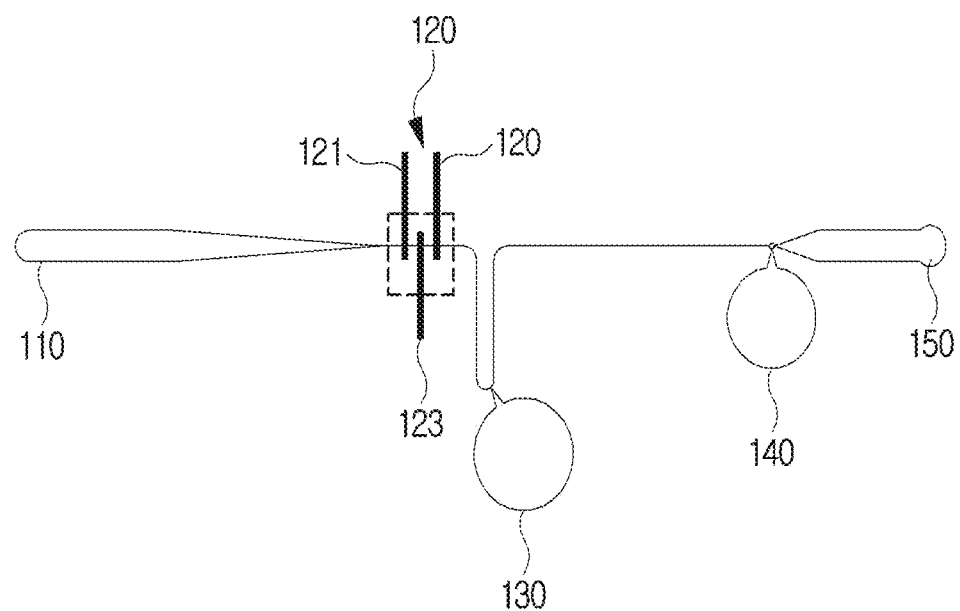
FIG. 3 is a schematic view of the single cell separating apparatus applied to FIG. 1.
Figure 4:
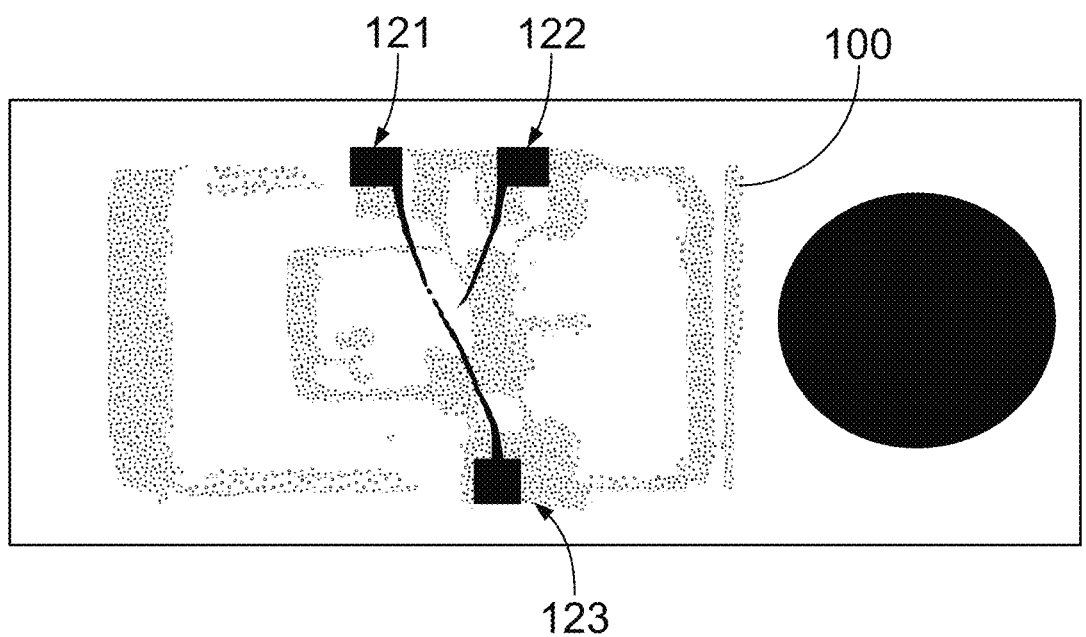
FIG. 4 is a view illustrating the single cell separating apparatus manufactured according to the exemplary embodiment of the present invention.
Figure 4:
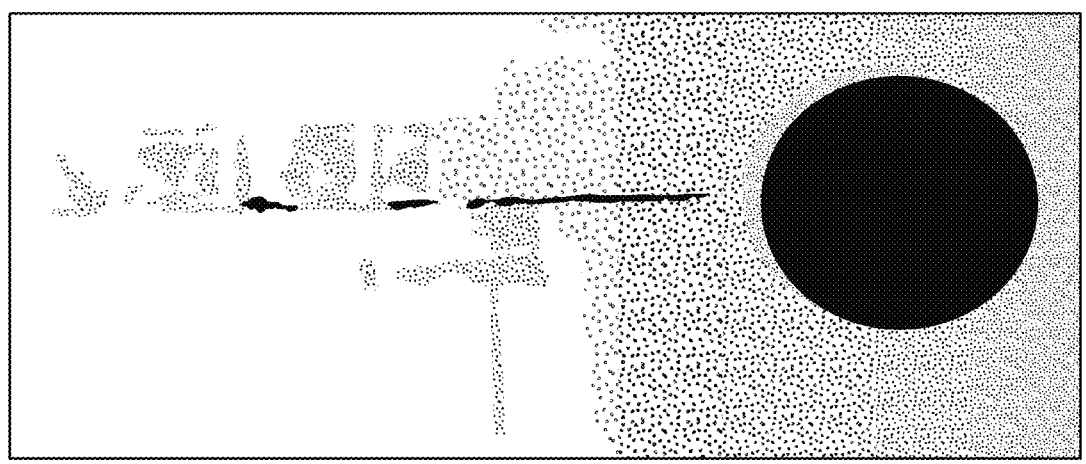
Figure 5:
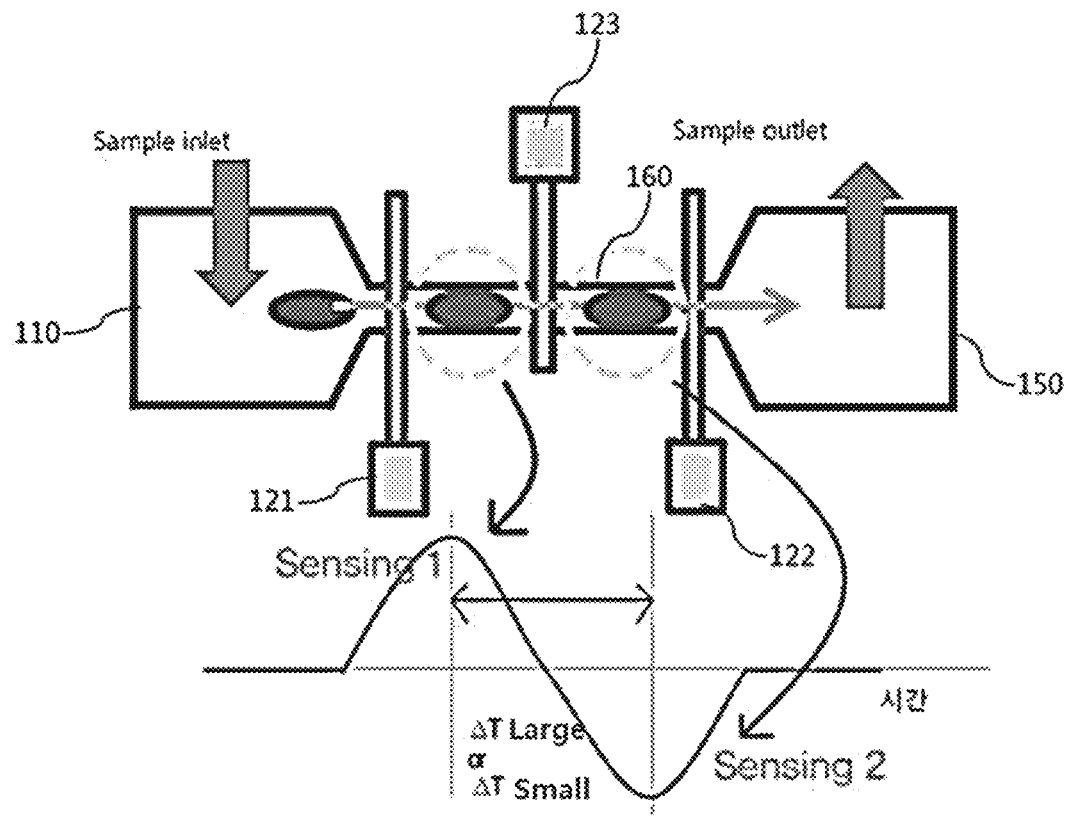
FIG. 5 is a view for explaining a process of measuring cell deformability in the single cell separating apparatus according to the present invention.
Figure 6:
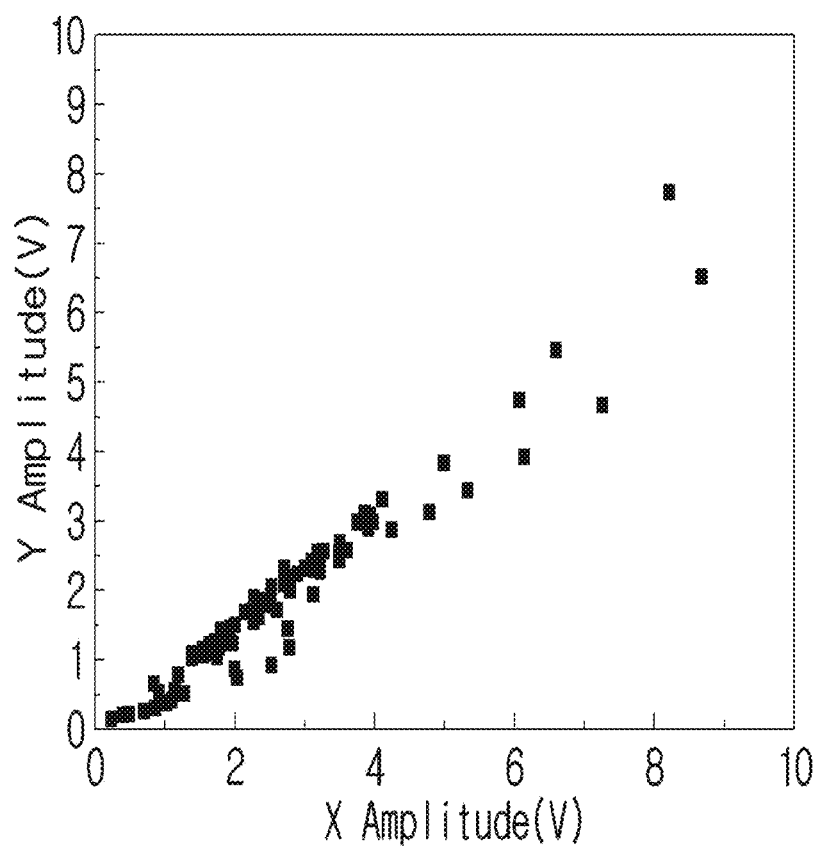
FIG. 6 is a graph in which detection signals, which are outputted from a detection electrode adopted in the present invention and received by a single cell separation control device adopted in FIG. 1, are displayed on X and Y axes.
Figure 7A:
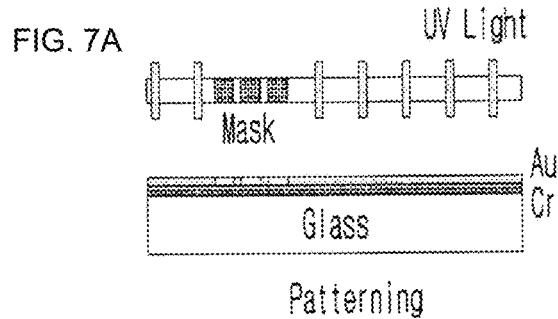
FIGS. 7A-7F are a view for explaining a process of manufacturing the single cell separating apparatus according to the present invention.
Figure 7B:
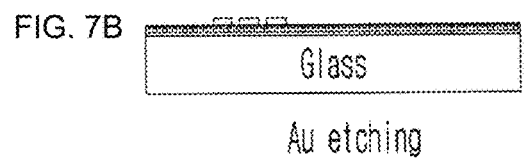
Figure 7C:
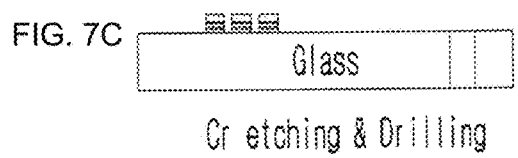
Figure 7D:
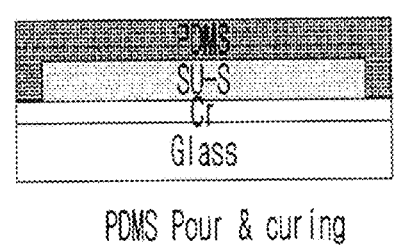
Figure 7E:
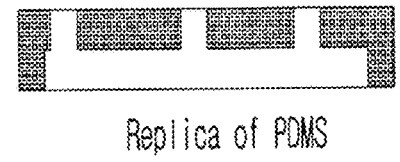
Figure 7F:
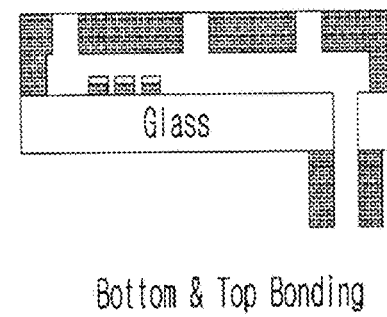

FIG. 1 is a block diagram for explaining a configuration of a single cell separating apparatus according to the present invention. FIG. 2 is a block diagram for explaining an exemplary embodiment of a single cell separating unit in FIG. 1. FIG. 3 is a schematic view of the single cell separating apparatus applied to FIG. 1. FIG. 4 is a view illustrating the single cell separating apparatus manufactured according to the exemplary embodiment of the present invention. FIG. 5 is a view for explaining a process of measuring cell deformability in the single cell separating apparatus according to the present invention. FIG. 6 is a graph in which detection signals, which are outputted from a detection electrode adopted in the present invention and received by a single cell separation control device adopted in FIG. 1, are displayed on X and Y axes. FIG. 7 is a view for explaining a process of manufacturing the single cell separating apparatus according to the present invention.

(Electrode Adopting Method)

As illustrated in FIG. 1, a single cell separating apparatus includes a single cell separating apparatus 100 and a single cell separation control device 200.

The single cell separating apparatus 100 creates a fluid flow by using a syringe pump in order to convey a sample, which is introduced through a sample inlet port 110 and includes single cells, through a flow path of a fluid channel 160. The single cell separating apparatus 100 detects an electrical signal of the sample being conveyed through the flow path of the fluid channel 160 and outputs a detection signal. The single cell separating apparatus 100 separates the cells included in the sample from the sample being conveyed through the flow path of the fluid channel 160 based on a single cell separation control signal inputted in response to the detection signal. The single cell separating apparatus 100 introduces the separated cells into fluid droplets and discharges the separated cells through a cell discharge port.

The single cell separation control device 200 receives the detection signal and recognizes that the cells are conveyed through the fluid channel. The single cell separation control device 200 creates a single cell separation control signal based on the perception result, and outputs the single cell separation control signal to the single cell separating apparatus 100. That is, as illustrated in FIG. 6, the single cell separation control device 200 receives the detection signals outputted from a detection electrode 123, and provides the detection signals on a screen while displaying the detection signals on X and Y axes. Therefore, the single cell separation control device 200 may measure a size of the cell and the number of cells.

As illustrated in FIG. 2, the single cell separating apparatus 100 includes the sample inlet port 110 through which the sample including the single cells is introduced by physical force applied from the outside, a single cell measuring unit 120 which detects an electrical signal applied to the sample being conveyed through the flow path of the fluid channel 160 and outputs the electrical signal to the cell separation control device 200 when the sample including the single cells is introduced through the sample inlet port 110 and the fluid channel 160, and a single cell separating unit 140 which introduces the single cells being conveyed through the fluid channel 160 into fluid droplets based on the single cell separation control signal and discharges the single cells through a single cell discharge port 150 to the outside.

In this case, the sample may be conveyed through the fluid channel by the fluid flow created by the syringe pump.

In particular, the single cell separating apparatus 100 further includes a buffer unit between the single cell measuring unit 120 and the single cell separating unit 140, and the buffer unit 130 mitigates noise that occurs when the cells are separated by the single cell separating unit 140 and introduced into the fluid droplets. In this case, as illustrated in FIG. 3, the buffer unit 130 has a "U" shape and thus has a long flow path, but the buffer unit 130 may have any shape as long as the buffer unit 130 has a long flow path having a shape such as a zigzag shape other than the "U" shape. An interior of the buffer unit 130 is filled with a small amount of air.

Further, the single cell separating apparatus 100 further includes a fluid supply unit 170 which is operated based on the single cell separation control signal from the single cell separation control device 200 and supplies a fluid to be coupled to the cells separated by the single cell separating unit 140.

As illustrated in FIGS. 2 and 3, the single cell measuring unit 120 includes first and second electrodes 121 and 122 which are positioned to be spaced apart from each other at a predetermined interval and apply electrical signals to the flow path of the fluid channel 160 by electric power supplied from the outside, and the detection electrode 123 which is provided between the first and second electrodes 121 and 122 and detects and outputs the electrical signals of the sample being conveyed through the flow path of the fluid channel 160. That is, the electrical signals are applied to the sample by the first and second electrodes 121 and 122, and the sample may be easily conveyed through the flow path of the fluid channel 160. The detection electrode 123 detects the electrical signals of the sample being conveyed through the flow path of the fluid channel 160 and outputs the electrical signals to the cell separation control device 200. The single cell separation control device 200 recognizes the single cells having only the electrical signals greater than a predetermined limit value among the electrical signals inputted to the detection electrode 123, and creates and outputs the single cell separation control signal for separating the recognized single cells. That is, the single cell separation control device 200 receives the electrical signal through the detection electrode 123, and when a value equal to or greater than the predetermined limit value is inputted, the single cell separation control device 200 recognizes that the cells are conveyed through the flow path of the fluid channel 160, and outputs the single cell separation control signal to the single cell separating unit 140.

As illustrated in FIG. 4, the first and second electrodes 121 and 122 and the detection electrode 123 are formed on a lower panel 10 that forms a fluid channel 160. Meanwhile, instead of the configuration in which the first and second electrodes 121 and 122 and the detection electrode 123 are formed on the lower panel 10 illustrated in FIG. 4, the first and second electrodes 121 and 122 and the detection electrode 123 may be formed on an upper panel or may be formed separately on the lower panel and the upper panel, respectively.

That is, as illustrated in FIG. 7, the single cell separating apparatus 100 is formed in the form of a chip, and the chip broadly has an electrode portion for electrical detection, and a polydimethylsiloxane (PDMS) portion for forming a fluid channel That is, the chip for separating the single cell is manufactured by a lithographic process, as illustrated in FIG. 7. In more detail, referring to FIG. 7, a Cr layer and an Au layer are sequentially stacked on a glass substrate and then patterned by using UV beams and a mask designed to form a desired electrode pattern on the glass substrate, the Au layer is primarily etched, the Cr layer is then etched, and a hole is formed in the glass substrate, thereby forming the cell discharge port.

Thereafter, the substrate and the PDMS, which has the fluid channel pattern formed on the upper glass substrate by using SU-8, are joined to the chip, which is manufactured by the lithographic process as simply described above, by using oxygen plasma ($O_2$ plasma) processing, and as a result, the single cell separating apparatus may be completely manufactured as illustrated in FIG. 4.

Because the processes of forming the electrode portion and the PDMS portion are publicly known technologies, detailed descriptions thereof will be omitted.

An operation of the single cell separating apparatus configured as described above will be described below.

As illustrated in FIGS. 1 to 5, the single cell separation control device 200 is connected to the single cell separating apparatus 100, the sample including the single cells is injected through the sample inlet port 110, and then electric power is applied to the electrodes 121 and 122, and as a result, the sample including the single cells is smoothly conveyed through the flow path of the fluid channel 160. That is, when the fluid flows at a constant speed by the syringe pump, the sample including the single cells begins to be smoothly conveyed through the fluid channel 160 through which the fluid flows constantly.

As illustrated in FIG. 5, when the sample including the single cells conveyed through the fluid channel 160 is conveyed to a position of the fluid channel 160 where the sample has passed through the first electrode 121, a voltage detected by the detection electrode 123 is outputted to the single cell separation control device 200, and the single cell separation control device 200 outputs, on the screen, the voltage inputted from the detection electrode 123 of the single cell separating apparatus 100, such that a sinusoidal signal is created, as illustrated in FIG. 5. In this case, when the cell is recognized as illustrated in FIG. 7, the cell separation control device displays the recognition on the X and Y axes so as to measure the size of the cell and count the number of cells, and may provide the size of the cell and the number of cells.

Then, the single cell separation control device 200 recognizes only values equal to or greater than the predetermined limit value (threshold) corresponding to a peak of the measured sinusoidal signal, thereby recognizing the single cells. When the single cell is recognized as described above, the single cell separation control device 200 generates the single cell separation control signal and outputs the single cell separation control signal to the fluid supply unit 170 connected to the single cell separating unit 140.

Then, the fluid supply unit 170 operates in response to the single cell separation control signal and discharges a small amount of already accommodated PBS, and the cells are introduced into the small amount of discharged PBS (phosphate buffer saline) and discharged to the outside through the single cell discharge port 150. That is, the fluid supply unit 170 pushes, with pressure, a small amount of fluid to the single cell separating unit 140 in response to the single cell separation control signal, and the single cell separating unit 140 allows the single cells to be in the pushed fluid droplets and then discharges the single cells through the single cell discharge port 150 to the outside of the chip which is the single cell separating apparatus 100. In this case, the buffer unit 130 performs a buffering operation so as to prevent an abnormal measurement state of the single cell measuring unit 120 which is caused by a reverse flow (backflow) generated by pressure generated by the fluid supply unit 170. Because an interior of the buffer unit 130 is filled with a small amount of air, the pressure generated by the fluid supply unit 170 is mitigated.

(Optical Measurement Sensor Adopting Method)

Figure 8:
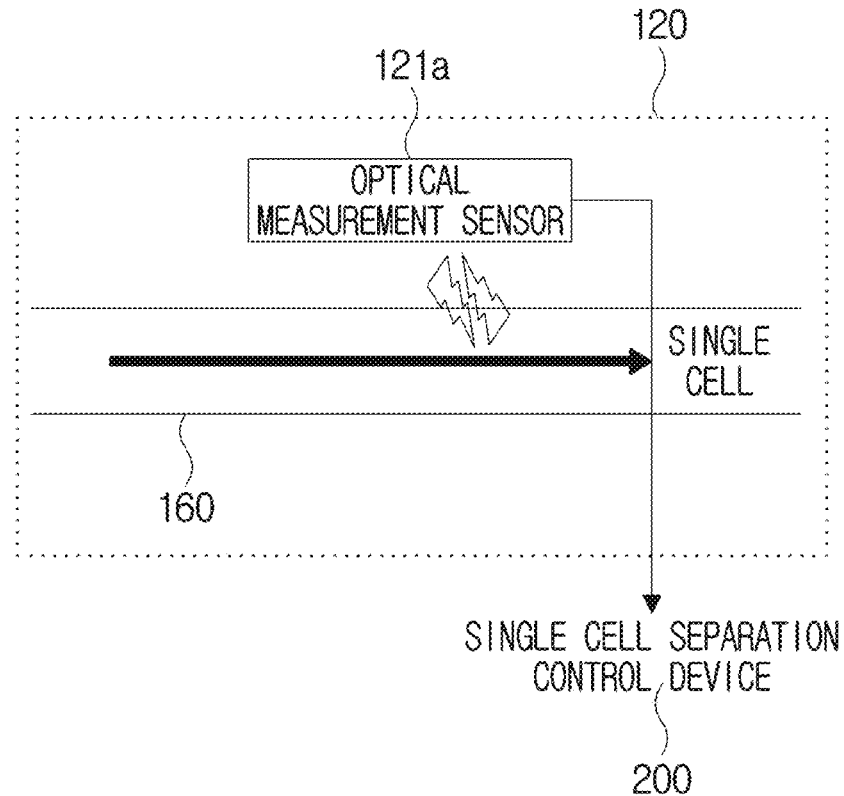
FIG. 8 is a block diagram for explaining another exemplary embodiment of the single cell separating unit in FIG. 1.

As another exemplary embodiment of the present invention, as illustrated in FIG. 8, a single cell separating apparatus includes a fluid channel 160 which has an upper panel and a lower panel and has a flow path which is formed between the upper panel and the lower panel and configured to convey a sample including single cells, and an optical measurement sensor 121a which serves as a single cell measuring unit, emits light to the fluid channel 160, receives light reflected by the sample including the single cells, converts the light into an electrical signal, and outputs the electrical signal, as a single cell detection signal, to a single cell separation control device 200.

Then, the single cell separation control device 200 derives a fluid channel passing speed of the sample including the single cells by using the electrical signal outputted from the optical measurement sensor 121a, and outputs a single cell separation control signal based on the passing speed of the sample.

In other words, a fluorescent bead attached to the single cell emits light by the light emitted from the optical measurement sensor 121a, and the optical measurement sensor 121a receives the light, converts the light into an electrical signal, and outputs the electrical signal. That is, the fluorescent bead is attached to the single cell in the sample, such that the optical measurement sensor 121a receives the light reflected by the fluorescent bead. Because a method of attaching the fluorescent bead to the sample is performed by an antigen-antibody reaction in the related art, a detailed description thereof will be omitted.

Therefore, the single cell separation control device 200 may derive a fluid channel passing speed of the sample including the single cells by using the electrical signal outputted from the optical measurement sensor 121a, create the single cell separation control signal based on the passing speed of the sample, and output the single cell separation control signal to the single cell separating unit 140.

Here, only differences from the electrode adopting method will be described, and descriptions of identical parts will be omitted.

(Hall Sensor Adopting Method)

Figure 9:
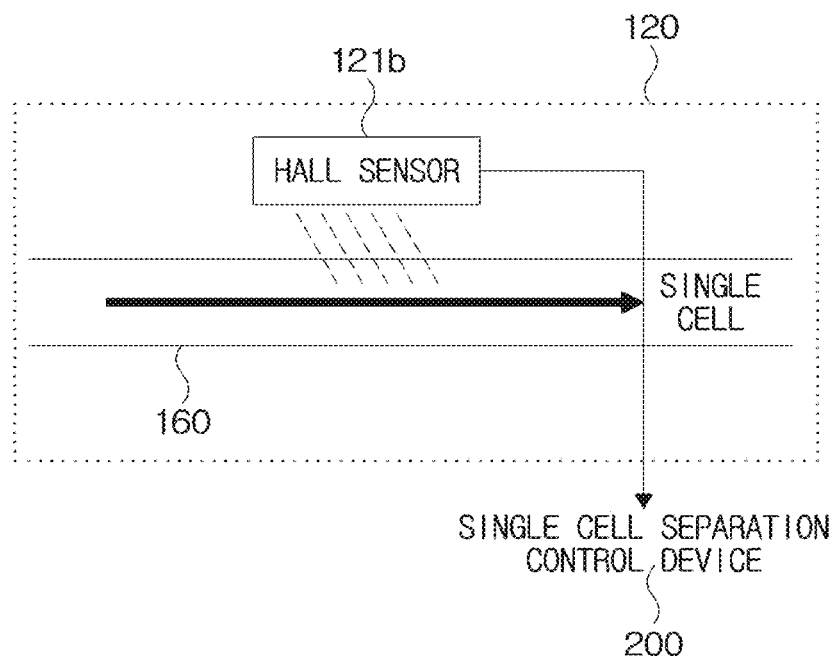
FIG. 9 is a block diagram for explaining still another exemplary embodiment of the single cell separating unit in FIG. 1.

As still another exemplary embodiment of the present invention, as illustrated in FIG. 9, a single cell separating apparatus includes a fluid channel 160 which has an upper panel and a lower panel and has a flow path which is formed between the upper panel and the lower panel and configured to convey a sample including single cells, a Hall sensor 121b which serves as a single cell measuring unit, applies a magnetic field to the fluid channel 160, and detects and outputs a voltage generated by the magnetic field, and a single cell separation control device 200 which derives a fluid channel passing speed of the sample including the single cells by receiving a voltage detected by the Hall sensor 121b, and outputs the single cell separation control signal based on the passing speed of the sample.

In other words, the Hall sensor 121b of the single cell measuring unit 120 applies a magnetic field to the fluid channel 160, detects a voltage generated by the magnetic field, and outputs the voltage to the single cell separation control device 200. The single cell separation control device 200 may derive the fluid channel passing speed of the sample including the single cells by receiving the voltage detected by the Hall sensor 121b, create the single cell separation control signal based on the passing speed of the sample, and output the single cell separation control signal to the single cell separating unit 140. That is, because particles having magnetism are attached to the single cells included in the sample, the particles having magnetism react with the magnetic field applied to the fluid channel of the Hall sensor 121b, and the Hall sensor 121b detects the resulting voltage and outputs the voltage to the single cell separation control device 200. Because a method of attaching the particles having magnetism to the single cells in the sample is performed by an antigen-antibody reaction in the related art, a detailed description thereof will be omitted.

Here, only differences from the electrode adopting method will be described, and descriptions of identical parts will be omitted.

Figure 10:
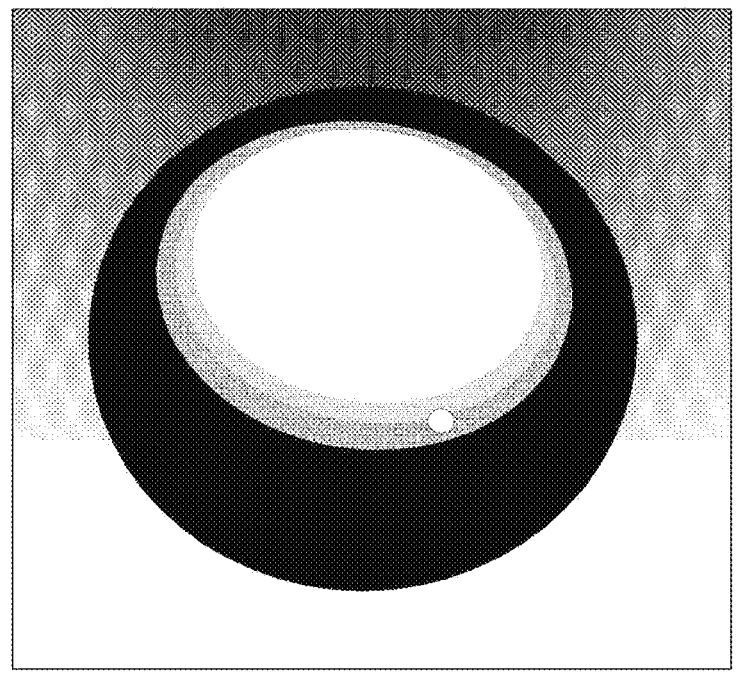
FIG. 10 is a view illustrating a result of separating a single cell according to the exemplary embodiment in FIG. 2.

FIG. 10 is a view illustrating a result of measuring fluid droplets which are created by using a basic electrical signal and dropped onto 96 wells. As illustrated in FIG. 10, it can be seen that one cell is present in one well.

Figure 11:
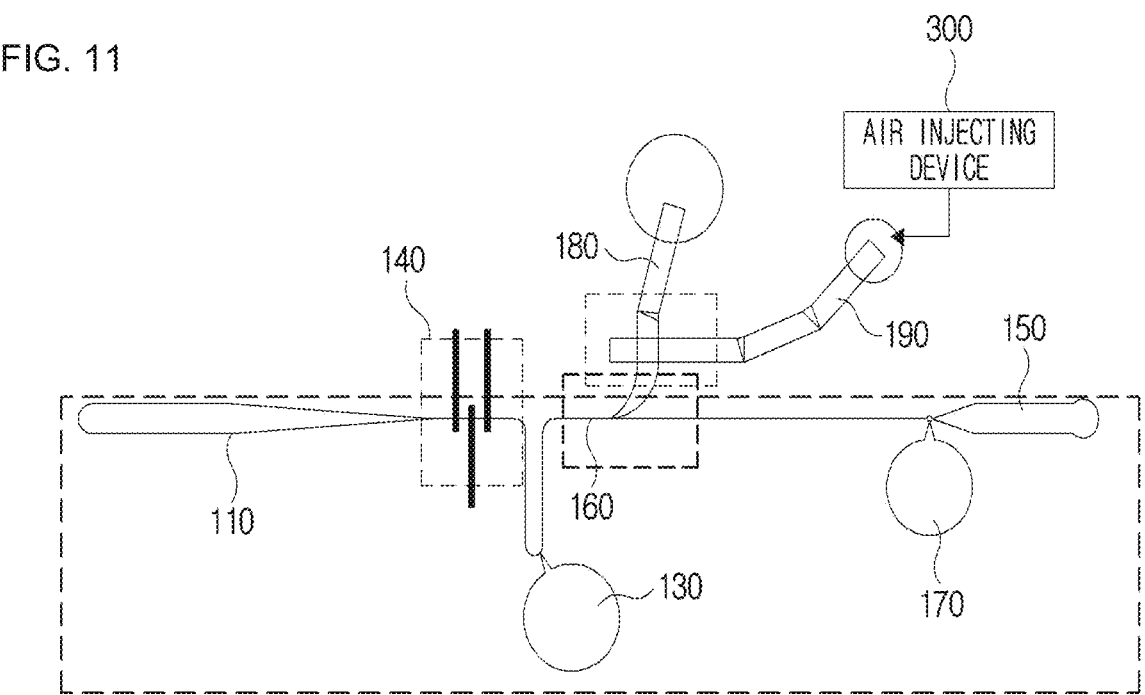
FIG. 11 is a view for explaining a state in which a heterologous cell separating channel and a valve channel are provided in FIG. 1.
Figure 12:
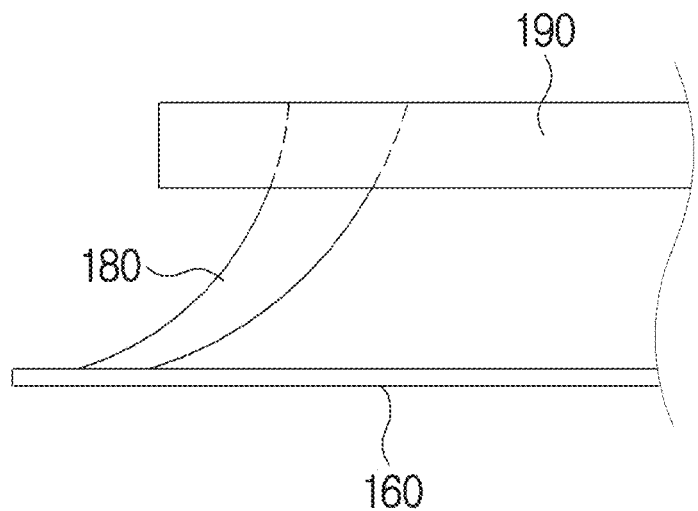
FIGS. 12 and 13 are views for explaining structural features of a fluid channel, the heterologous cell separating channel, and the valve channel adopted in the present invention.
Figure 13:
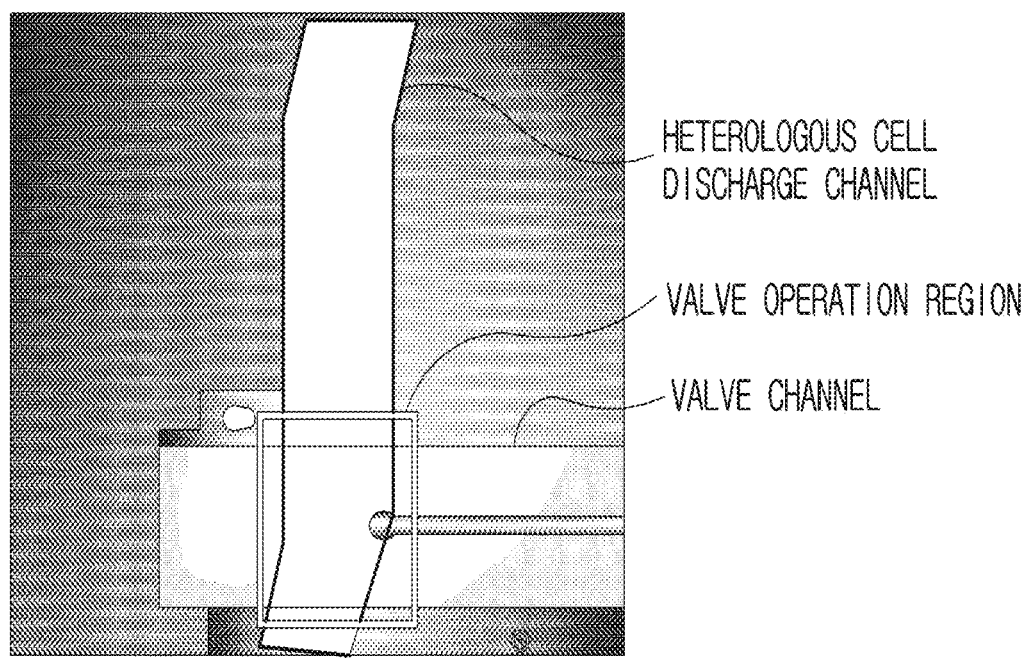

FIG. 11 is a view for explaining a state in which a heterologous cell separating channel and a valve channel are provided in FIG. 1. FIGS. 12 and 13 are views for explaining structural features of the fluid channel, the heterologous cell separating channel, and the valve channel adopted in the present invention. FIG. 14 is a view for explaining a PDMS membrane adopted in the present invention. FIG. 15 is a view for explaining a well plate adopted in the present invention.

(Adoption of Heterologous Cell Separation Function)

The single cell separating apparatus according to the present invention adopts a structural feature capable of separating and discharging heterologous cells (including white blood cells, red blood cells, debris, etc.) and single cells (cancer cells).

As illustrated in FIGS. 11 to 13, the structural feature for separating and discharging the heterologous cell and the single cell includes a heterologous cell discharge channel 180 which has one end portion connected to the fluid channel 160 and discharges the heterologous cell to the outside when the heterologous cell moving through the fluid channel 160 is detected by the single cell measuring unit 120, and a valve channel 190 which has one end portion provided in the heterologous cell discharge channel 180 and the other end portion is connected to an air injecting device 300 for injecting air into the heterologous cell discharge channel 180.

The fluid channel 160 and the heterologous cell discharge channel 180 are configured to have different tube thicknesses, and at normal times, the fluid flows toward a portion having low resistance.

Further, an interior of the tube of the valve channel 190 is filled with air. That is, the air injecting device 300 is connected to one end portion of the valve channel 190, such that the air injecting device 300 injects air into the valve channel 190, as necessary. That is, when the desired single cell is detected by the single cell measuring unit 140 of the single cell separating apparatus, the single cell separating apparatus outputs the single cell detection signal to the single cell separation control device 200, and the single cell separation control device 200 controls the air injecting device 300 to inject air into the tube of the valve channel 190, such that a PDMS membrane 195, which is provided between the valve channel 190 and the heterologous cell discharge channel 180, is expanded as illustrated in FIG. 14B, thereby blocking the fluid flowing to the heterologous cell discharge channel 180 and changing a direction of the fluid.

(Well Plate for Separating and Storing Single Cell and Heterologous Cell)

Lastly, the single cell separating apparatus according to the present invention further includes a well plate which stores the heterologous cells and the single cells separated by the single cell separating apparatus. As illustrated in FIG. 15, the well plate 400 has multiple spaces, a first space 410 stores the heterologous cell, and the remaining multiple spaces 420 separate and store the single cells, one space for each single cell.

Figure 15A:
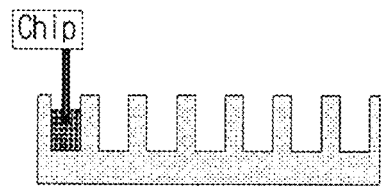
FIGS. 15A-15F are a view for explaining a well plate adopted in the present invention.

During an initial operation, the well plate 400 is stopped in a state in which the well plate 400 is moved so that a cell discharge portion is positioned in the first space (see FIG. 15A). Further, when the single cell measuring unit 140 recognizes that the heterologous cell is introduced into the fluid channel 160, the valve channel 190 allows the fluid channel 160 and the heterologous cell discharge channel 180 to be connected to each other, and the heterologous cell, which flows through the heterologous cell discharge channel 180, is discharged into the first space of the well plate 400 in a state in which in response to control of the single cell separation control device 200, a well plate driving unit 200 moves the web plate 400 so that a first compartment of the well plate 400 is positioned below a heterologous cell discharge port of the single cell separating apparatus 100 (see FIG. 15A).

In a case in which the single cell measuring unit 140 recognizes that the single cell is introduced into the fluid channel 160, the air injecting device 300 is controlled to inject air into the valve channel 190, and the PDMS membrane 195 is expanded to block the heterologous cell discharge channel 180, such that the single cell is discharged to the single cell discharge port 150 through the fluid channel 160. In this case, the single cell separation control device 200 controls the well plate driving unit 430 to discharge the single cell into a second space and store the single cell in the second space. Further, under the control of the single cell separation control device 200, the well plate driving unit 430 moves the well plate 400 so that the first space is positioned below the heterologous cell discharge channel 180 of the single cell separation control device 400 (see FIG. 15B). That is, when the single cell is discharged and stored into a corresponding space of the well plate 400, the first space is positioned again below the heterologous cell discharge valve 180 (see FIG. 15C).

Figure 15D:
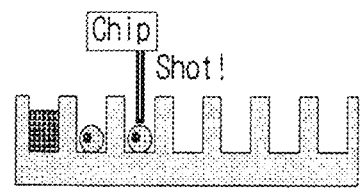
Figure 15B:
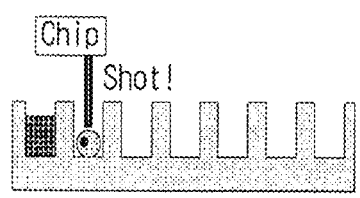
Figure 15E:
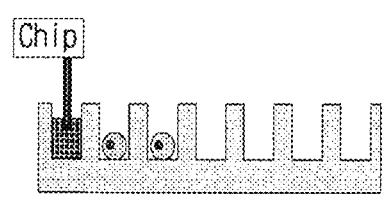
Figure 15C:
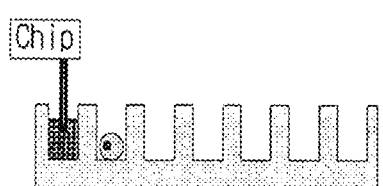
Figure 15F:
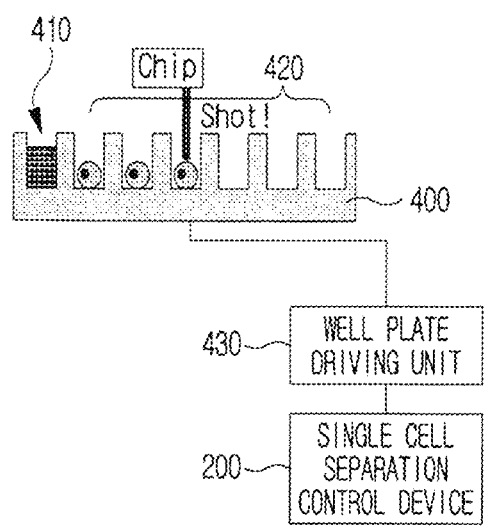
Figure 15F:

As described above, the well plate driving unit 430 moves forward or rearward by being controlled by the single cell separation control device 300, such that only the heterologous cells are separated and stored in the first space, and the single cells are discharged and stored in the remaining spaces, that is, the second space, a third space, and so on in the order in which the single cells are discharged (see FIGS. 15D to 15F).

The aforementioned contents can be modified and changed by those skilled in the art to which the present invention pertains without departing from the essential features of the present invention. Therefore, the exemplary embodiments of the present invention are provided for illustrative purposes only but not intended to limit the technical concept of the present invention. The scope of the technical concept of the present invention is not limited thereto. The protective scope of the present invention should be construed based on the following claims, and all the technical spirit in the equivalent scope thereto should be construed as falling within the scope of the present invention.

The invention claimed is:

1. A single cell separating apparatus comprising:
   a fluid channel which has an upper panel and a lower panel and has a flow path which is formed between the upper panel and the lower panel and configured to convey a sample including a single cell;
   a single cell measuring unit comprising an operative electrode pair comprising first and second electrodes provided along the fluid channel and spaced apart from each other at a predetermined interval in a direction of the flow path, said operative electrode pair being operative to work collectively to apply an electrical signal to the sample being conveyed through the flow path of the fluid channel, and a detection electrode which is provided between the first electrode and the second electrode in the direction of the flow path and detects the single cell in the sample being conveyed through the flow path, such that the single cell measuring unit applies a first electrical signal to the sample being conveyed through the flow path, detects a second electrical signal of the sample to which the first electrical signal is applied, and detects whether there is the single cell in the sample; and
   a single cell separation control device which outputs a single cell separation control signal when the single cell is detected by the detection electrode.

2. The single cell separating apparatus of claim 1, wherein the first electrode and the second electrode are provided on the upper panel, the lower panel, or the upper and lower panels of the fluid channel.

3. The single cell separating apparatus of claim 1, wherein the single cell separation control device counts and provides the number of single cells passing through the flow path based on the second electrical signal inputted from the detection electrode.

4. The single cell separating apparatus of claim 1, further comprising:
   a buffer unit in fluid communication with the fluid channel, the buffer unit defining a flow path having a shape reducing a reverse flow caused by air pressure created when supplying the fluid to be coupled to the single cell.

5. The single cell separating apparatus of claim 4, wherein the buffer unit has an elongated flow path between two points that is longer than a linear distance between said two points.

6. The single cell separating apparatus of claim 1, further comprising:
a heterologous cell discharge channel which has one end portion connected to the fluid channel and discharges a heterologous cell from the single cell separating apparatus when the heterologous cell is detected in the fluid channel by the single cell measuring unit; and
a valve channel which has one end portion provided in the heterologous cell discharge channel and the other end portion connected to an air injecting unit for injecting air into the heterologous cell discharge channel.

7. The single cell separating apparatus of claim 6, wherein the fluid channel and the heterologous cell discharge channel have different tube thicknesses.

8. The single cell separating apparatus of claim 6, wherein a PDMS membrane is formed between the heterologous cell discharge channel and the valve channel.

9. The single cell separating apparatus of claim 1, wherein the well plate has multiple spaces, a first space stores heterologous cells, and the remaining multiple spaces separate and store the single cells, one space for each single cell.

10. A single cell separating apparatus comprising:
a fluid channel having an upper panel and a lower panel cooperating to define a flow path configured to convey a sample including a single cell;
a single cell measuring unit comprising:
an electrode pair comprising first and second electrodes provided adjacent the fluid channel, said first and second electrodes being provided to be spaced apart from each other at a predetermined interval in a direction of the flow path, said first and second electrodes being operatively coupled and controlled to operate to work collectively to apply a particular electrical signal to the sample conveyed through the flow path of the fluid channel to create an electrical field; and
a detection electrode provided adjacent the fluid channel at a location between the first electrode and the second electrode in the direction of the flow path, said detection electrode being operable to detect changes in the electrical field as the single cell in as the sample is conveyed through the flow path, such that the single cell measuring unit applies the electrical field to the sample being conveyed through the flow path, detects another electrical signal corresponding to changes in the electrical field of the sample as it is conveyed though the flow path, and thereby detects whether there is the single cell in the sample in the flow path; and
a single cell separation control device operable to output a single cell separation control signal when the single cell is detected by the detection electrode.

11. A single cell separating apparatus comprising:
a fluid channel defining a flow path configured to convey a sample including a single cell;
a single cell measuring unit comprising:
an operative electrode pair having first and second electrodes provided adjacent the fluid channel, said first and second electrodes being provided to be spaced apart from each other at a predetermined interval in a direction of the flow path, said first and second electrodes of said operative electrode pair being operatively coupled and configured to work collectively as a single working electrode pair to collectively apply a first electrical signal as the sample is conveyed through the flow path of the fluid channel; and
a detection electrode provided adjacent the fluid channel at a location between the first electrode and the second electrode in the direction of the flow path, said detection electrode being operable to detect a second electrical signal associated with the sample in response to the sample passing said first electrode; and
a single cell separation control device operable to output a single cell separation control signal when the single cell is detected by the detection electrode.

* * * * *